United States Patent [19]

Saito et al.

[11] Patent Number: 4,879,386
[45] Date of Patent: Nov. 7, 1989

[54] ANTI-TUMOR DC-52 COMPOUNDS

[75] Inventors: Hiromitsu Saito, Sagamihara; Yoichi Uosaki; Akira Sato, both of Machida; Tadashi Hirata, Yokohama; Makoto Morimoto, Shizuoka; Tadashi Ashizawa, Numazu, all of Japan

[73] Assignee: Kyowa Hakko Kogyo Co., Ltd., tokyo, Japan

[21] Appl. No.: 207,639

[22] PCT Filed: Sep. 28, 1987

[86] PCT No.: PCT/JP87/00708

§ 371 Date: May 25, 1988

§ 102(e) Date: May 25, 1988

[87] PCT Pub. No.: WO88/02369

PCT Pub. Date: Apr. 7, 1988

[30] Foreign Application Priority Data

Oct. 1, 1986 [JP] Japan .................. 61-233801

[51] Int. Cl.$^4$ .................. A61K 31/495; C07D 471/18; C07D 498/22
[52] U.S. Cl. .................. 544/343
[58] Field of Search .................. 544/343

[56] References Cited

U.S. PATENT DOCUMENTS 4,650,869  3/1987  Hirata et al. .................. 544/343

FOREIGN PATENT DOCUMENTS 0157126  10/1985  European Pat. Off. .

OTHER PUBLICATIONS

Translation of Claims of Japanese Unexamined Pat. Application 170189/82.

Primary Examiner—Mark L. Berch
Attorney, Agent, or Firm—Fitzpatrick, Cella, Harper & Scinto

[57] ABSTRACT

The present invention relates to novel derivatives of DC-52 represented by the following formula (I):

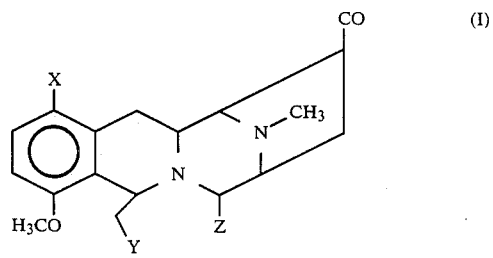

ps [wherein X is chlorine, bromine, iodine, hydroxyl, formyl, hydroxyiminomethyl, cyano, nitro, amino or lower alkanoylamino; and Y is hydroxyl and Z is cyano, or Y and Z represent —O— in the form of —Y—Z—]. These compounds and pharmacologically acceptable salts thereof have high anti-tumor activity.

1 Claim, No Drawings

ANTI-TUMOR DC-52 COMPOUNDS

TECHNICAL FIELD

The present invention relates to novel DC-52 derivatives having anti-tumor activity.

BACKGROUND ART

DC-52 is an antibiotic represented by the following formula:

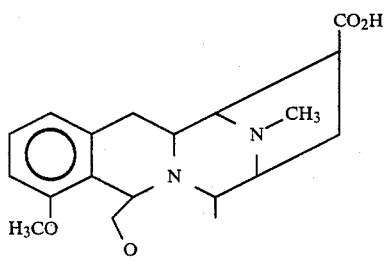

It shows antibacterial activity against a variety of bacteria, and also has anti-tumor activity against lymphocytic leukemia P-388 and the like (Japanese Published Unexamined Patent Application No. 170189/82).

As a derivative thereof, DX-52-1 represented by the following formula and having anti-tumor activity is known (Japanese Published Unexamined Patent Application No. 210086/84).

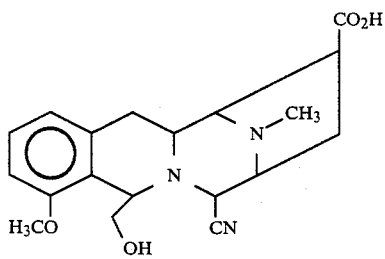

Derivatives of DC-52 having higher anti-tumor activity are always in demand, as is the case with other types of anti-tumor antibiotics.

DISCLOSURE OF THE INVENTION

The derivatives of DC-52 of the present invention having high anti-tumor activity are compounds represented by the following formula (I):

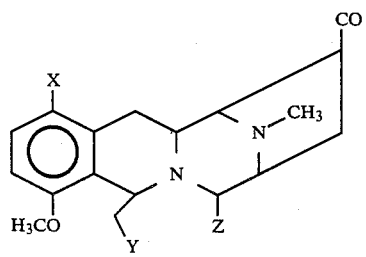

wherein X is chlorine, bromine, iodine, hydroxyl, formyl, hydroxyiminomethyl, cyano, nitro, amino or lower alkanoylamino; and Y is hydroxyl and Z is cyano, or Y and Z represent —O— in the form of —Y—Z— [The compounds are hereinafter referred to as compounds (I). The same shall apply to compounds of other formula Nos.].

The lower alkanoylamino in the definition of X in formula (I) means a straight chain or branched alkanoylamino group having 1 to 4 carbon atoms such as formamide, acetamide, propionamide, butyramide and isobutyramide.

Pharmacologically acceptable salts of compounds (I) have high anti-tumor activity as well as compounds (I). These salts include pharmacologically acceptable acid addition salts, alkali metal salts, alkaline earth metal salts, ammonium salts and pharmacologically acceptable organic base addition salts. The pharmacologically acceptable acid addition salts include pharmacologically acceptable inorganic acid addition salts such as hydrochloride, hydrobromide, hydroiodide, sulfate, phosphate and nitrate; and pharmacologically acceptable organic acid addition salts such as acetate, benzoate, maleate, fumarate, succinate, tartrate, citrate, oxalate, glyoxylate, aspartate, methanesulfonate, ethanesulfonate, propanesulfonate, methanedisulfonate, α, β-ethanedisulfonate and benzenesulfonate. The alkali metal salts include sodium salt, potassium salt, etc. and the alkaline earth metal salts include calcium salt, magnesium salt, etc. The pharmacologically acceptable organic base addition salts include salts with ethanolamine, triethylamine, morpholine, piperidine, etc.

The process for preparing compounds (I) is described below.

Compounds represented by the following formula (I-1) are prepared by reaction of DX-52-1 with a halogenating agent in an inert solvent:

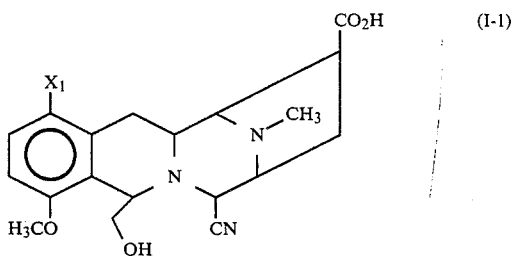

(wherein $X_1$ is chlorine, bromine or iodine).

Chlorination is carried out usually at 0° to 80° C. for one to eight hours using chlorine, N-chlorosuccinimide or the like as the chlorinating agent, and acetic acid, DMF or the like as the inert solvent.

Bromination is carried out usually at 0° to 50° C. for one to six hours using bromine, N-bromosuccinimide or the like as the brominating agent, and acetic acid, DMF or the like as the inert solvent.

Iodination is carried out usually at 20° to 80° C. for one to eight hours using iodine-periodic acid as the iodinating agent, and water, acetic acid or the like as the inert solvent.

Compounds of formula (I) in which X is formyl or hydroxyiminomethyl, Y is hydroxyl and Z is cyano can be prepared by the following reaction steps:

DX-52-1 ⟶

-continued

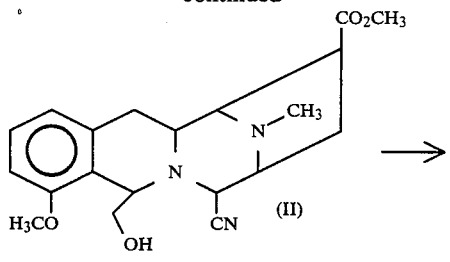

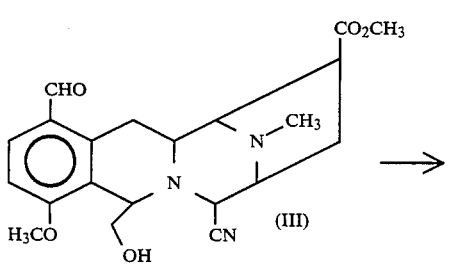

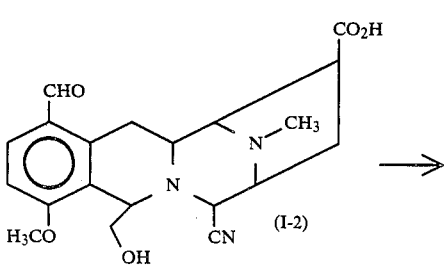

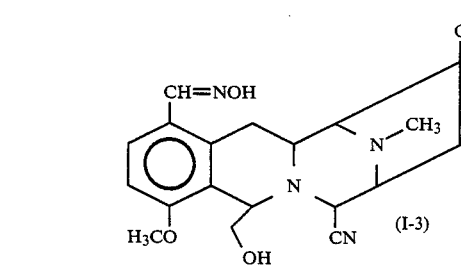

DX-52-1 is first esterified with methanol in the presence of an acid catalyst to form compound (II). The acid catalyst includes mineral acids such as hydrogen chloride and sulfuric acid and Lewis acids such as $BF_3$-$OEt_2$, and is usually used in an amount of 2 to 20 equivalents based on DX-52-1. The reaction is usually carried out at 20° to 60° C. and is complete in 3 to 24 hours. Compound (II) may also be prepared by dropwise addition of a diethyl ether solution of diazomethane to a solution of DX-52-1 in an inert solvent (e.g., methanol, ethanol, tetrahydrofuran, chloroform and methylene chloride, either alone or in combination). The reaction is continued at 0° to 40° C. until the generation of nitrogen gas ceases (usually for 30 minutes to 3 hours).

Compound (II) thus obtained is allowed to react with α, α-dichloromethyl methyl ether in an inert solvent in the presence of a Lewis acid to give compound (III). α, α-dichloromethyl methyl ether is used in an amount of 1.2 to 2.5 equivalents based on compound (II). The inert solvent includes haloalkanes such as methylene chloride and chloroform. Lewis acid includes titanium tetrachloride, aluminum chloride, etc., and is used in an amount of 3 to 5 equivalents based on compound (II). The reaction is usually carried out at 0° to 50° C. and is complete in several to 24 hours.

Compound (III) is then hydrolyzed with an alkali in a solvent to form compound (I-2). The alkali includes sodium hydroxide, potassium hydroxide, etc. and is usually used in an amount of 2 to 6 equivalents based on compound (III). As the solvent, water, methanol, ethanol, tetrahydrofuran, dioxane, dimethoxyethane and others may be used, either alone or in combination. The reaction is usually carried out at 0° to 50° C. and is complete in 1 to 20 hours.

Compound (I-3) is obtained by reaction of compound (I-2) with hydroxylamine hydrochloride in an inert solvent. The hydroxylamine hydrochloride is usually used in an amount of about 1.5 equivalents based on compound (I-2), but the amount may be increased up to about 5 equivalents to accelerate the reaction. As the inert solvent, methanol, ethanol, tetrahydrofuran and others may be used either alone or in combination. The reaction is usually carried out at 0° to 40° C. and is complete in one to several hours.

Compound of formula (I) in which X and Z are cyano and Y is hydroxyl can be prepared by the following reaction steps.

(III) ⟶

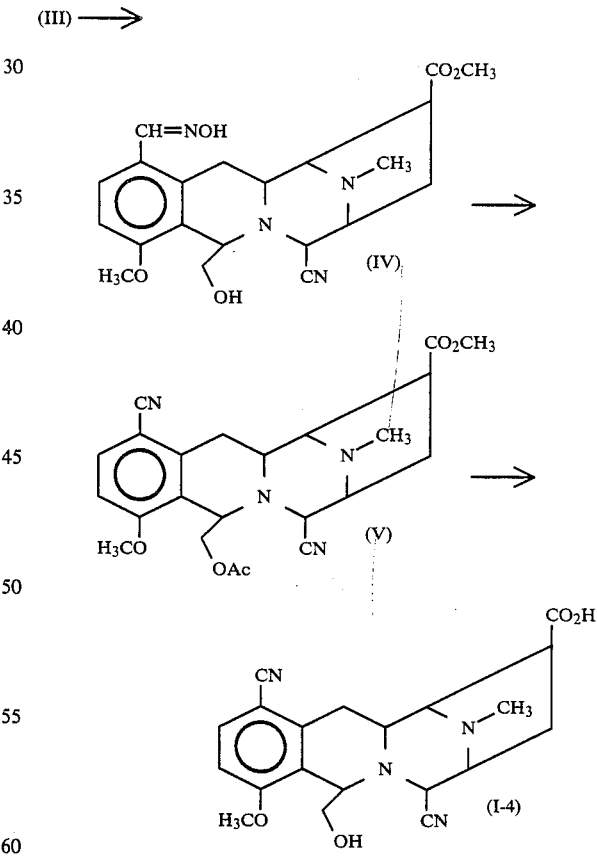

Compound (III) is subjected reaction with hydroxylamine hydrochloride in the same manner as in the above step of (I-2)→(I-3) to form compound (IV).

Compound (IV) thus obtained is heated in acetic anhydride to form compound (V). The reaction is usually carried out at 100° to 150° C. and is complete in one to several hours.

Compound (V) is then converted to compound (I-4) in the same manner as in the above step of (III)→(I-2).

Compound of formula (I) in which X and Y are hydroxyl and Z is cyano can be prepared by the following reaction steps:

(III) →

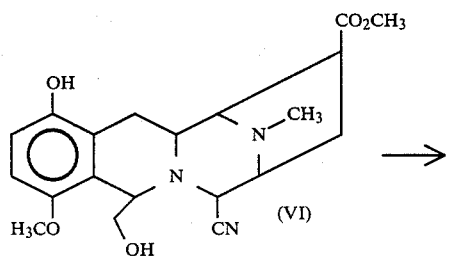

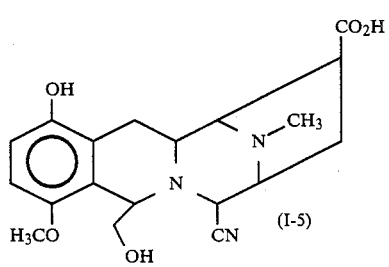

Reaction of compound (III) with hydrogen peroxide and sulfuric acid in an inert solvent gives compound (VI) (Baeyer-Villiger reaction). Hydrogen peroxide and sulfuric acid are usually used in amounts of 1 to 2 equivalents and 1 to 5 equivalents, respectively, based on compound (III). The inert solvent includes methanol, ethanol, acetonitrile, etc. The reaction is usually carried out at 0° to 40° C. and is complete in several to 10 hours.

Compound (VI) thus obtained is then converted to compound (I-5) in the same manner as in the above step of (III)→(I-2).

Compound of formula (I) in which X is nitro, Y is hydroxyl and Z is cyano can be prepared by the following reaction steps:

DX-52-1 →

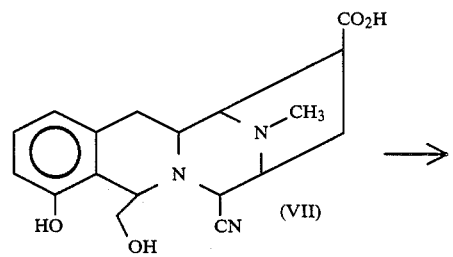

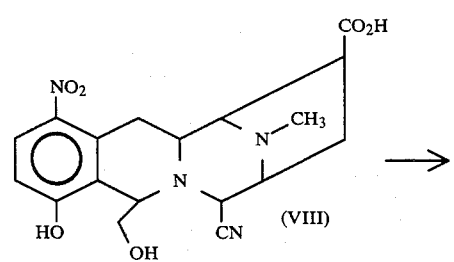

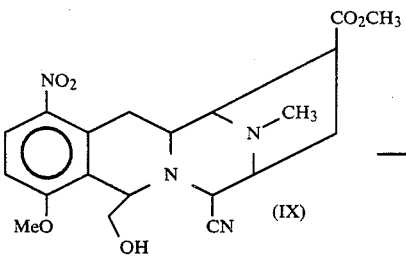

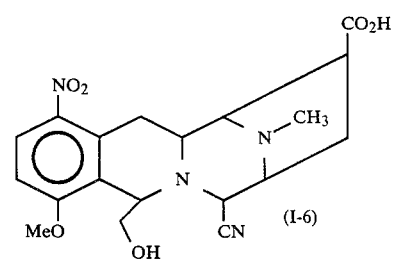

DX-52-1 is allowed to react with a demethylating agent in an inert solvent to form compound (VII). The demethylating agent includes boron tribromide, boron trichloride, aluminum chloride-ethanethiol, etc. and is usually used in an amount of 3 to 7 equivalents based on DX-52-1. The inert solvent includes haloalkanes such as methylene chloride and chloroform and aromatic hydrocarbons such as toluene. The reaction is carried out at −78° to 30° C. and is usually complete in several to 48 hours.

Compound (VII) thus obtained is nitrated with nitric acid in acetic acid to give compound (VIII). Nitric acid is usually used in an amount of 1 to 3 equivalents based on compound (VII). The reaction is usually carried out at 10° to 50° C. and is complete in 2 to 10 hours.

Compound (VIII) is then methylated with diazomethane under the same conditions as in the above step of DX-52-1→(II) to form compound (IX). Compound (IX) is finally hydrolyzed under the same conditions as in the above step of (III)→(1-2) to obtain compound (I-6).

Compound of formula (I) in which X is amino, Y is hydroxyl and Z is cyano can be prepared by the following reaction steps:

(IX) →

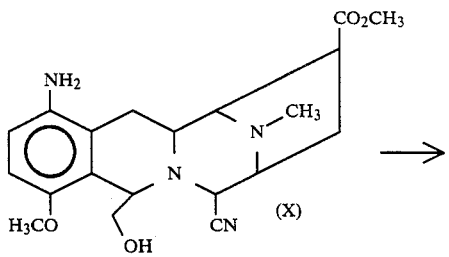

-continued

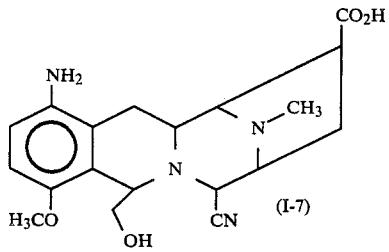

Compound (IX) is subjected to catalytic hydrogenation in an inert solvent to form compound (X). The catalyst includes Pd-C, PtO2, etc. and is usually used in an amount of 20 to 40% (W/W) based on compound (IX). As the inert solvent, methanol, ethanol, tetrahydrofuran, dioxane and others may be used either alone or in combination. The reaction is usually carried out at 10° to 50° C. and is complete in 1 to 10 hours.

Compound (X) is then hydrolyzed under the same conditions as in the above step of (III)→(I-2) to obtain compound (I-7).

Compounds of formula (I) in which X is lower alkanoylamino, Y is hydroxyl and Z is cyano can be prepared by the following reaction steps:

(X) →

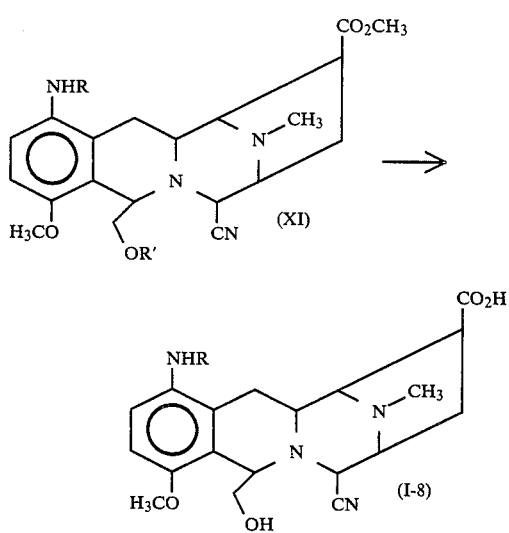

(wherein R is lower alkanoyl, and R' is hydrogen or lower alkanoyl).

Compound (X) is allowed to react with a reactive derivative of lower alkanecarboxylic acid represented by formula (XII):

ROH    (XII)

[wherein R is as defined in formula (XI)], in the presence of an inert solvent and a base if necessary, to give compound (XI). The reactive derivative includes acid chloride, acid anhydride, active esters (e.g., p-nitrophenyl ester and N-oxysuccinimide ester), mixed acid anhydrides (mixed acid anhydrides with monoethyl carbonate, monoisobutyl carbonate, etc.) and the like and is usually used in an amount of 1 to 3 equivalents based on compound (X). When the reactive derivative also serves as the reaction solvent, it may be used in large excess. As the inert solvent, methylene chloride, chloroform, toluene, tetrahydrofuran, pyridine, acetonitrile and others may be used either alone or in combination. The base includes pyridine, triethylamine, dimethylaminopyridine, etc. and is usually used in an amount of 1 to 3 equivalents based on compound (X). The reaction is usually carried out at 0° to 50° C. and is complete in 1 to 24 hours.

Compound (XI) thus obtained is then hydrolyzed under the same conditions as in the above step of (III)→(I-2) to obtain compound (I-8).

Compounds of formula (I) in which Y and Z represent —O— in the form of —Y—Z— [hereinafter referred to as compounds (I-9)]can be prepared by subjecting compound (I) in which Y is hydroxyl and Z is cyano to reaction in water or an organic solvent in the presence of a silver salt, followed by treatment with water or hydrochloric acid if necessary. The organic solvent includes acetonitrile, methanol, ethanol, tetrahydrofuran, dioxane, etc., which are used either alone or in combination, and the silver salt includes silver nitrate, silver chlorate, silver perchlorate, silver fluoride, etc. The silver salt is usually used in one equivalent based on compound (I) in which Y is hydroxyl and Z is cyano, but the amount may be increased up to about 3 equivalents to accelerate the reaction and enhance the yield of compound (I-9). The reaction is usually carried out at 0° to 30° C. and is complete in 0.5 to several hours.

Compounds (I-9) can also be prepared by subjecting compound (I) in which Y is hydroxyl and Z is cyano to reaction in water or a mixture of water and a hydrophilic solvent in the presence of hydrogen chloride.

Hydrochloric acid is usually used at a concentration of 0.1 to 12N. The hydrophilic solvent includes methanol, ethanol, tetrahydrofuran, etc. The reaction is usually carried out at room temperature to 100° C. and is complete in 1 to 24 hours.

Compounds (I-9) are present in the form of (I-9') in a water-containing solvent.

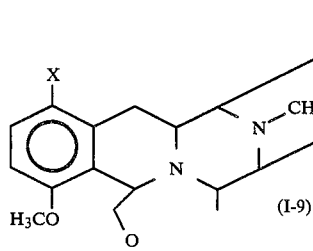 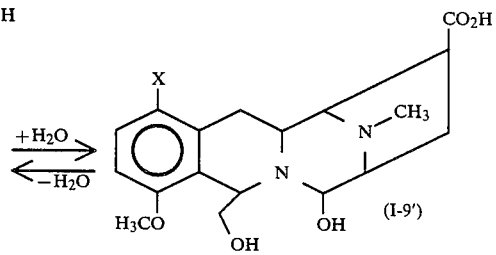

In each of the reactions described above, the final product can be purified by concentrating the reaction mixture under reduced pressure, or extracting the reaction mixture with a water-immiscible solvent (e.g., ethyl acetate and chloroform) and concentrating the extract under reduced pressure, and subjecting the residue thus obtained to column chromatography using silica gel, HP20 resin or HP20SS resin (Mitsubishi Chemical Industries Ltd.).

Compounds (I) and pharmacologically acceptable salts thereof have high anti-tumor activity against lymphocytic leukemia P-388 and the like, and are hence expected to be useful as anti-tumor agents for mammals including human beings. The pharmacological activities of compounds (I) are described below referring to Experimental Examples.

EXPERIMENTAL EXAMPLE 1

Anti-tumor activity

Table 1 shows the anti-tumor activity of typical compounds of formula (I) against lymphocytic leukemia P-388.

TABLE 1

| Compound | Dose (mg/kg) | T/C (%) | Compound | Dose (mg/kg) | T/C (%) |
|---|---|---|---|---|---|
| 1 | 12.5 | 123 | 6 | 25 | 124 |
| 2 | 12.5 | 140 | 7 | 200 | 138 |
| 4 | 12.5 | 150 | 9 | 25 | 140 |
| 5 | 50 | 131 | 11 | 25 | 142 |

$$T/C(\%) = \frac{\text{Mean survival days for the test groups}}{\text{Mean survival days for the control group}} \times 100$$

The experiment was carried out in the following manner.

Five male CDF mice each having a weight of about 22 g were used for each group as test animals, and $1 \times 10^6$ cells of lymphocytic leukemia P-388 tumor were implanted intraperitoneally into the test animals. After 24 hours, 0.2 ml of phosphate-buffered physiological saline containing a test compound was administered once intraperitoneally. The life-prolonging effect of the compound was represented by T/C.

EXPERIMENTAL EXAMPLE 2

Acute toxicity

Five day mice were used for each group as test animals, and each test compound was administered once intraperitoneally to the respective groups of animals. $LD_{50}$ was calculated from the death-rate of each group according to the method of Behrens-Kölber. The result is shown in the table below.

| Compound | 1 | 3 | 5 | 9 | 10 |
|---|---|---|---|---|---|
| $LD_{50}$ (mg/kg) | 50 | 50 | 100 | >100 | >50 |

Compounds (I) and pharmacologically acceptable salts thereof can be used as an anti-tumor composition, singly or, in general, together with at least one pharmacologically acceptable additive. For example, compound (I) or a salt thereof is dissolved in physiological saline or an aqueous solution of glucose, lactose, mannitol, etc. to prepare a pharmaceutical composition suitable for injection. Alternatively, injectable powder can be prepared by freeze-drying compound (I) or a salt thereof in a usual way and adding sodium chloride thereto. The pharamaceutical compositions of the present invention may also contain additives which are well known in the pharmaceutical field, such as pharmaceutically acceptable salts. Suitable dose of these compositions may vary with the age, conditions and other factors of patients, but is usually in the range of 0.003 to 1 mg/kg/day as compound (I) for mammals including human beings. The administration is effected, for example, once a day (by single administration or consecutive administration), or intermittently one to three times a week or once every two or three weeks, by intravenous injection. If desired, the compositions can be orally administered at the same dose and in the same manner. For oral administration, they are given as tablets, capsules, powders, granules, ampules, etc., which contain additives well known in the field of pharmaceutics. If desired, intra-arterial administration, intraperitoneal administration, intra-thoracic administration, etc. are also possible at the same dose and in the same manner as above.

The anti-tumor compositions of the present invention are expected to be effective for the treatment of leukemia, stomach cancer, large intestinal carcinoma, lung cancer, breast cancer, uterine carcinoma and similar diseases of mammals including human beings.

EXAMPLES

Table 2 shows the structures and compound Nos. of typical compounds (I).

TABLE 2

[Structure with substituents X, Y, Z on bicyclic system with $CO_2H$, $N$-$CH_3$, $H_3CO$ groups]

| Compound | X | Y | Z |
|---|---|---|---|
| 1 | Cl | OH | CN |
| 2 | Cl | O | |
| 3 | Br | OH | CN |
| 4 | Br | O | |
| 5 | I | OH | CN |
| 6 | I | O | |
| 7 | CHO | OH | CN |
| 8 | CH=NOH | OH | CN |
| 9 | CN | OH | CN |
| 10 | CN | O | |
| 11 | OH | OH | CN |
| 12 | $NO_2$ | OH | CN |
| 13 | NHAc | OH | CN |

The physicochemical data given in the following Examples were measured using the instruments listed below.

IR: Nippon Bunko, IR-810
NMR: Varian, EM-390 (90 MHz) Nippon Denshi, FX-100 (100 MHz) Bruker, AM400 (400 MHz)
MS: Hitachi, B-80

EXAMPLE 1

Synthesis of compound 1

<Sodium salt of DX-52-1 (113 mg) was dissolved in 1.5 ml of acetic acid, and 3.4 ml of 1.3 M solution of chlorine in acetic acid was added dropwise at room temperature. The mixture was stirred at room temperature for one hour. The reaction mixture was then concentrated under reduced pressure to remove acetic acid, and the residue was dissolved in water. The solution was adjusted to pH 8 by addition of an aqueous solution of sodium hydrogen carbonate and subjected to chromatography (Diaion HP-20, 12 ml; water:methanol = 1:0–0:1) to obtain 86.6 mg (70%) of compound 1 as sodium salt.

$^1$H NMR (CD$_3$OD: ppm): 7.24 (d, 1H), 6.81 (d, 1H), 5.27 (d, 1H), 5.18 (dd, 1H), 3.83 (s, 3H), 2.4–3.7 (m, 9H), 2.33 (s, 3H), 2.07 (dd, 1H.

IR (KBr; cm$^{-1}$):
3410, 2950, 1650, 1558, 1465, 1394, 1277, 1259, 1075
MS (EI Me ester):
374, 376 (M+).

EXAMPLE 2

Synthesis of compound 2

To 366 mg of sodium salt of compound 1 was added 7 ml of concentrated hydrochloric acid, and the mixture was heated at 50° C. for 2.5 hours with stirring. After cooling, the reaction mixture was subjected to chromatography (Diaion HP-20, 40 ml; water:methanol = 1:0–1:1) to obtain 143 mg (44%) of compound 2.

$^1$H NMR (CD$_3$OD: ppm): 7.70 (d, 1H), 6.69 (d, 1H), 4.59 (d, 1H), 4.54 (dd, 1H), 4.22 (s, 1H), 4.16 (m, 1H), 3.83 (s, 3H), 3.66 (dd, 1H), 3.55 (dd, 1H), 3.41 (d, 1H), 3.39 (dd, 1H), 2.93 (dd, 1H), 2.82 (s, 3H), 2.69 (dd, 1H), 2.64 (m, 1H), 2.51 (dd, 1H).

IR (KBr; cm$^{-1}$): 3600–2400, 3410, 1585, 1470, 1385, 1290, 1265, 1090, 810
MS (SIMS; m/z): 365 and 367 (MH)+.

EXAMPLE 3

Synthesis of compound 3

Sodium salt of DX-52-1 (700 mg) was dissolved in 10 ml of acetic acid, and 2.03 ml of 1M solution of bromine in acetic acid was added dropwise, followed by stirring at room temperature. 1M solution of bromine in acetic acid was further added three times (0.4 ml, 140 minutes later; 0.3 ml, 80 minutes further later; and 0.2 ml, 90 minutes further later), and the mixture was stirred at room temperature for an additional 50 minutes. The reaction mixture was then concentrated, and the concentrate was adjusted to pH 7.3 by addition of an NaHCO$_3$ solution. The resulting solution was subjected to chromatography (Diaion HP-20SS, 110 ml; water:methanol = 1:0–1:2) to obtain 478 mg (56.5%) of compound 3 as sodium salt.

$^1$H NMR (CD$_3$OD: ppm):
7.40 (d, 1H), 6.77 (d, 1H), 4.30 (d, 1H), 4.22 (m, 1H), 3.83 (s, 3H), 3.40–3.80 (m, 4H), 2.43–3.20 (m, 5H), 2.33 (s, 3H), 2.15 (m, 1H).

$^{13}$C NMR (D$_2$O; ppm):
184.2, 155.8, 137.1, 132.1, 124.8, 119.6, 114.9, 111.6, 70.4, 65.0, 65.0, 58.6, 58.4, 58.1, 56.4, 45.4, 42.0, 33.6, 30.1.
MS (SIMS; m/z):
458, 460 (M+1)+.

EXAMPLE 4

Synthesis of compound 4

Sodium salt of compound 3 (308 mg) was dissolved in 5 ml of concentrated hydrochloric acid, and the solution was stirred at 50° C. for three hours. After cooling, the reaction mixture was subjected to chromatography (Diaion HP-20, 20 ml; water:methanol = 1:0–1:1) to obtain 106.8 mg (37.0%) of compound 4.

$^1$H NMR (D$_2$O; ppm):
7.50 (d, 1H, J=8.9Hz), 6.85 (d, 1H, J=8.9Hz), 4.95 (d, 1H, J=3.3Hz), 4.48 (m, 1H), 4.27 (bs, 1H), 3.98 (m, 1H), 3.82 (s, 3H), 3.63 (dd, 1H, J=11.4, 3.3Hz), 3.55 (dd, 1H, J=9.5, 4.6Hz), 3.53 (dd, 1H, J=11.4, 4.8Hz), 3.45 (m, 1H), 3.09 (dd, 1H, J=15.4, 2.5Hz), 2.81 (s, 3H), 2.57 (m, 2H), 2.46 (dd, 1H, J=14.2, 10.6Hz).

$^{13}$C NMR (D$_2$O; ppm):
179.4, 156.0, 136.2, 132.2, 125.7, 114.7, 112.1, 81.8, 71.6, 70.0, 65.7, 56.5, 54.5, 53.6, 41.1, 40.6, 32.4, 27.4.
MS (EI Me ester; m/z): 422, 424 M+.

EXAMPLE 5

Synthesis of compound 5

Sodium salt of DX-52-1 (504 mg) was dissolved in a mixture of 10 ml of acetic acid, 2 ml of water and 0.3 ml of concentrated sulfuric acid. To the solution were added 337 mg of iodine and 151 mg of periodic acid dihydrate, and the mixture was heated at 65° C. for 75 minutes with stirring. After the reaction mixture was cooled, 1.9 ml of 5N aqueous solution of sodium hydroxide was added, and the resulting solution was concentrated under reduced pressure. The residue was dissolved in 3 ml of saturated aqueous solution of sodium hydrogen carbonate, and 4 ml of 5N aqueous solution of sodium hydroxide was added to raise the pH to 11 or above. Then, 2 g of sodium thiosulfate was added, and the resulting solution was subjected to chromatography (Diaion HP-20, 100 m±; water:methanol = 1:0–1:1) to obtain 402 mg (60%) of compound 5 as sodium salt.

$^1$H NMR (CD$_3$OD; ppm): 7.67 (d, 1H), 6.63 (d, 1H), 4.27 (d, 1H), 4.20 (dd, 1H), 3.83 (s, 3H), 3.8–2.4 (m, 9H), 2.34 (s, 3H), 2.08 (dd, 1H)

IR (KBr; cm$^{-1}$) 3420, 2946, 1559, 1461, 1394, 1276, 1258, 1075.
MS (EI Me ester: m/z): 497 M+, 466 (M-OMe)+.

EXAMPLE 6

Synthesis of compound 6

Sodium salt of compound 5 (329 mg) was dissolved in a mixture of 6 ml of methanol and 6 ml of acetonitrile, and 121 mg of silver nitrate was added to the solution, followed by stirring at room temperature for two hours. The reaction mixture was concentrated under reduced pressure, and 4 ml of 1N hydrochloric acid was added to the residue. After the precipitate was filtered off, the filtrate was subjected to chromatography (Diaion HP-20, 40 ml; water:methanol = 1:0–1:1) to obtain 152 mg (51%) of compound 6.

$^1$H NMR (CD$_3$OD; ppm):
7.28 (d, 1H), 6.89 (d, 1H), 4.62 (d, 1H), 4.55 (dd, 1H), 4.28 (s, 1H), 4.25 (m, 1H), 3.84 (s, 3H), 3.75 (dd, 1H), 3.70 (dd, 1H), 3.47 (d, 1H), 3.43 (dd, 1H), 3.11 (dd, 1H), 2.85 (s, 3H), 2.7–2.5 (m, 3H).

IR (KBr; cm$^{-1}$):
3700–2400, 3400, 2960, 1725, 1580, 1465, 1280, 1265, 1090, 810.
MS (SIMS; m/z):
457 (MH)+, 331.

EXAMPLE 7

Synthesis of compound 7

Compound b obtained in Reference Example 2 (301 mg) was dissolved in 9 ml of methanol, and 6 ml of water and 3 ml of 1N sodium hydroxide solution were added. The mixture was stirred at room temperature for four hours, and 1N hydrochloric acid was added to adjust the pH to about 4. The resulting solution was concentrated, and the concentrate was subjected to chromatography (Diaion HP-20, 30 ml; water:methanol=1:0-1:1) to obtain 252 mg (86.7%) of compound 7.

$^1$H NMR (CD$_3$OD: ppm): 10.04 (s, 1H), 7.77 (d, 1H), 7.03 (d, 1H), 4.28 (d, 1H), 4.23 (m, 1H), 3.99 (s, 3H), 3.40-3.87 (m, 4H), 3.53 (bs, 1H), 2.43-2.97 (m, 4H), 2.34 (s, 3H), 2.12 (dd, 1H).

MS (SIMS; m/z): 386 (M+1)$^+$.

EXAMPLE 8

Synthesis of compound 8

Compound 7 obtained in Example 7 (90 mg) was dissolved in 2 ml of methanol, and 81 mg of hydroxylamine hydrochloride was added. The mixture was stirred at room temperature for 40 minutes. The reaction mixture was concentrated, and the concentrate was subjected to chromatography (Diaion HP-20, 10 ml; water:methanol=0-3:2) to obtain 78.3 mg (83.7%) of compound 8.

1H NMR (D20; ppm): 8.32 (s, 1H), 7.50 (d, 1H, J=8.7Hz), 6.92 (d, 1H, J=8.7Hz), 4.79 (d, 1H, J=2.5Hz), 4.49 (m, 1H), 4.43 (bs, 1H), 4.33 (dd, 1H, J=5.4, 2.8Hz), 3.83 (s, 3H), 3.73 (m, 1H), 3.72 (dd, 1H, J=11.5, 2.8Hz), 3.55 (dd, 1H, J=11.5, 5.5Hz), 3.26 (m, 1H), 3.13 (dd, 1H, J=15.6, 2.5Hz), 2.92 (s, 2H), 2.83 (m, 1H), 2.69 (dd, 1H, J=15.5, 11.5Hz), 2.58 (dd, 1H, J=14.6, 10.6Hz).

IR (KBr; cm$^{-1}$) 3380, 1708, 1599, 1490, 1462, 1268.

$^{13}$C NMR (D$_2$O, ppm): 177.1, 157.8, 150.5, 135.2, 128.5, 122.41, 122.38, 116.6, 110.6, 71.1, 66.0, 65.7, 57.6, 57.1, 56.5, 56.4, 41.1, 28.8, 28.6.

MS (SIMS; m/z): 401 (M+1)$^+$, 374.

EXAMPLE 9

Synthesis of compound 9

Compound d obtained in Reference Example 4 (489 mg) was dissolved in 10 ml of methanol, and 5 ml of water and 4.5 ml of 1N sodium hydroxide solution were added. The mixture was stirred at room temperature for 18 hours. The reaction mixture was concentrated, and the concentrate was subjected to chromatography (Diaion HP-20, 60 ml; water:methanol =1:0-9:1) to obtain 350 mg (77%) of compound 9 as sodium salt.

$^1$H NMR (D$_2$O; ppm): 7.63 (d, 1H, J=8.7Hz), 6.94 (d, 1H, J=8.7Hz), 4.27 (d, 1H, J=2.8Hz), 4.16 (m, 1H), 3.87 (s, 3H), 3.72 (dd,1H, J=11.7, 2.8Hz), 3.67 (dd, 1H, J=11.7, 3.9Hz), 3.61 (m, 1H), 3.60 (bs, 1H), 3.12 (dd, 1H, J=10.0, 5.4Hz), 3.00 (dd, 1H, J=15.3, 2.2Hz), 2.90 (bd, 1H, J=11.5Hz), 2.74 (dd, 1H, J=15.3, 11.5Hz), 2.55 (m, 1H), 2.26 (s, 3H), 2.06 (dd, 1H, J=13.5, 10.0Hz).

$^{13}$C NMR (D$_2$O; ppm): 184.2, 160.3, 142.0, 134.6, 124.1, 119.8, 119.7, 110.5, 103.0, 70.5, 65.1, 64.1, 58.5, 58.2, 57.8, 56.7, 45.4, 42.0, 31.9, 30.2

MS (SIMS; m/z): 405 (M+1)$^+$, 383, 356.

EXAMPLE 10

Synthesis of compound 10

Sodium salt of compound 9 obtained in Example 9 (100 mg) was dissolved in 3 ml of acetonitrile, and 46 mg of silver nitrate was added, followed by stirring at room temperature for one hour. Silver nitrate (25 mg) was further added, and the mixture was stirred at room temperature for an additional one hour. An acetate buffer solution (pH 4.0) was added, and the insoluble matters were filtered off. The filtrate was concentrated, and the concentrate was subjected to chromatography (Diaion HP-20, 15 ml; water:methanol=1:0-2:1) to obtain 70.8 mg (80.6%) of compound 10.

$^1$H NMR (D$_2$O; ppm): 7.64 (d, 1H, J=8.7Hz), 6.99 (d, 1H, J=8.7Hz), 4.95 (d, 1H, J=3.3Hz), 4.48 (m, 1H), 4.26 (bs, 1H), 3.98 (m, 1H), 3.89 (s, 3H), 3.68 (dd, 1H, J=11.5, 3.2Hz), 3.59 (dd, 1H, J=11.5, 4.4Hz), 3.51 (bd, 1H, J=11.3Hz), 3.43 (dd, 1H, J=10.5, 5.3Hz), 3.02 (dd, 1H, J=15.3, 2.4Hz), 2.81 (s, 3H), 2.75 (dd, 1H, J=15.2, 11.9Hz), 2.57 (m, 1H), 2.43 (dd, 1H, J=14.2, 10.6Hz).

$^{13}$C NMR (D$_2$O; ppm): 180.3, 160.3, 140.8, 134.5, 124.8, 119.6, 110.7, 102.8, 81.7, 71.7, 69.9, 65.0, 56.6, 54.3, 53.1, 41.7, 40.5, 30.7, 27.7.

MS (SIMS; m/z): 356 (M+1)$^+$.

EXAMPLE 11

Synthesis of compound 11

Compound e obtained in Reference Example 5 (200 mg) was dissolved in 4 ml of methanol, and 2 ml of water and 2 ml of 1N sodium hydroxide solution were added. The mixture was stirred at room temperature for six hours and adjusted to pH 8-8.5 by addition of 1N hydrochloric acid. The resulting mixture was concentrated, and the concentrate was subjected to chromatography (Diaion HP-20, 30 ml; water:methanol=1:0-9:1) to obtain 145 mg (73.2%) of compound 11 as sodium 1H NMR (D$_2$0; ppm): 6.82 (s, 2H), 4.24 (d, 1H, J=2.9Hz), 4.12 (m, 1H), 3.78 (s, 3H), 3.70 (dd, 1H, J=11.5, 3.0Hz), 3.62 (dd, 1H, J=11.5, 4.5Hz), 3.58 (m, 1H), 3.54 (bs, 1H), 3.13 (dd, 1H, J=9.9, 5.6Hz), 2.89 (dd, 1H, J=15.4, 2.5Hz), 2.77 (bd, 1H, J=11.1Hz), 2.53 (m, 1H), 2.35 (dd, 1H, J=15.3, 11.5Hz), 2.23 (s, 3H), 2.05 (dd, 1H, J=13.4, 10.0Hz).

$^{13}$C NMR (D$_2$O; ppm): 184.5, 150.4, 147.1, 125.8, 124.3, 119.7, 115.2, 111.3, 70.8, 65.2, 65.1, 58.8, 58.5, 58.3, 57.1, 45.4, 41.9, 30.1, 27.0.

MS (SIMS; m/z): 396 (M+1)$^+$, 374, 347.

EXAMPLE 12

Synthesis of compound 12

Compound h obtained in Reference Example 8 (134 mg) was dissolved in a mixture of 2 ml of tetrahydrofuran and 0.4 ml of methanol, and 2.6 ml of 0.5N sodium hydroxide solution was added. The mixture was stirred at room temperature for 2.5 hours. The reaction mixture was concentrated, and the concentrate was subjected to chromatography (Diaion HP-20, 15 ml; water:methanol=1:0-9:1) to obtain 100 mg (73.8%) of compound 12 as sodium salt.

$^1$H NMR (CD$_3$OD; ppm): 8.00 (d, 1H), 7.00 (d, 1H), 4.30 (m, 2H), 3.98 (s, 3H), 3.32-3.88 (m, 4H), 2.44-3.20 (m, 5H), 2.34 (s, 3H), 2.08 (m, 1H).

IR (KBr; cm$^{-1}$): 3400-3450, 1647, 1586, 1559, 1512, 1471, 1395, 1348, 1272

MS (SIMS; m/z): 425 (M+1)$^+$.

EXAMPLE 13

Synthesis of compound 13

Compound j obtained in Reference Example 9 (74 mg) was dissolved in 2 ml of methanol, and 2 ml of water and 0.89 ml of 1N sodium hydroxide solution were added. The mixture was stirred at room temperature for three hours and the pH was adjusted to about 4 by addition of 1N hydrochloric acid. The resulting mixture was concentrated, and the concentrate was subjected to chromatography (Diaion HP-20, 10 ml; water:methanol=1:0–1:1) to obtain 44.7 mg (68.6%) of compound 13.

$^1$H NMR (D$_2$O; ppm): 7.17 (d, 1H, J=8.8Hz), 6.96 (d, 1H, J=8.8Hz), 4.72 (d, 1H, J=2.5Hz), 4.38 (m, 1H), 4.31 (dd, 1H, J=4.9, 2.9Hz), 4.23 (bs, 1H), 3.85 (s, 3H), 3.76 (dd, 1H, J=11.6, 2.9Hz), 3.65 (dd, 1H, J=11.6, 5.0Hz), 3.47 (dd, 1H, J=10.5, 5.5Hz), 3.14 (m, 1H), 2.83 (s, 3H), 2.81 (m, 1H), 2.75 (m, 1H), 2.53 (dd, 1H, J=15.3, 11.4Hz), 2.46 (dd, 1H, J=14.4, 10.6Hz), 2.18 (s, 3H).

$^{13}$C NMR (D$^2$O; ppm): 179.7, 174.9, 155.6, 133.4, 127.8, 126.9, 122.7, 116.9, 110.7, 71.8, 66.1, 65.3, 57.8, 57.1, 56.6, 56.5, 42.7, 41.0, 29.4, 27.9, 22.6.

MS (SIMS; m/z): 415 (M+1)$^+$.

The structures and compound Nos. of the compounds obtained in the following Reference Examples are shown below. In the following, the structural formula

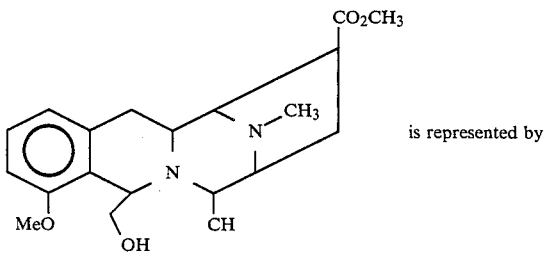

is represented by

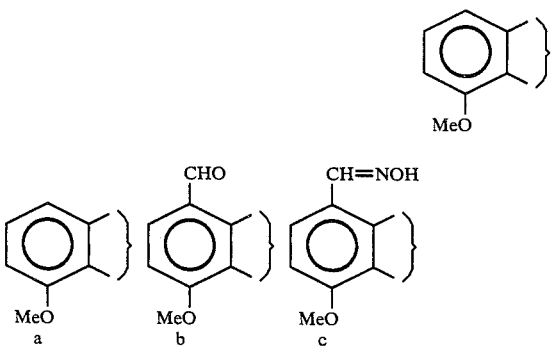

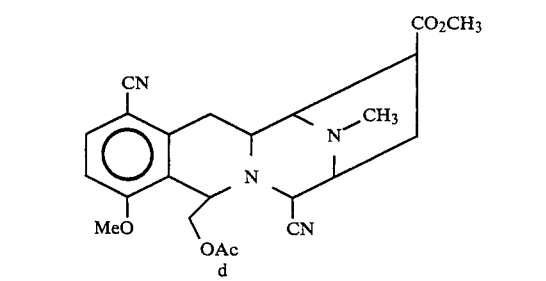

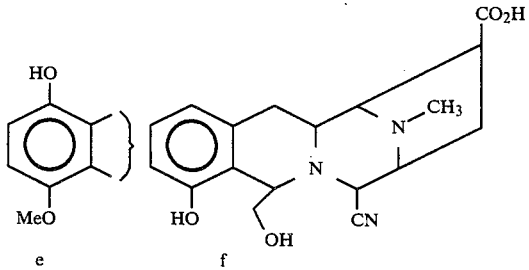

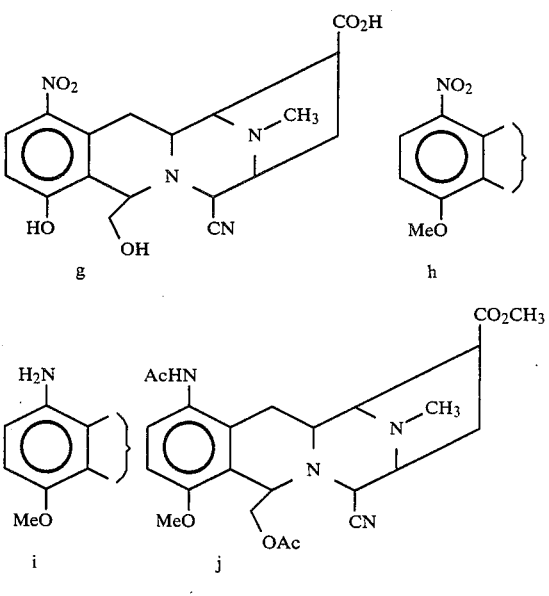

REFERENCE EXAMPLE 1

Synthesis of compound a

Sodium salt of DX-52-1 (500 mg) was dissolved in of methanol, and 1.5 ml of BF$_3$.OEt$_2$ was added. The mixture was stirred at room temperature for 18 hours, then at 40° C. for eight hours, and again at room temperature for hours. The reaction mixture was concentrated, and ethyl acetate and an aqueous solution of sodium hydrogen carbonate were added to the concentrate. The separated organic layer was washed with saturated aqueous solution of sodium chloride and dried over anhydrous sodium sulfate. Evaporation of the solvent gave 433 mg (88.4%) of compound a.

$^1$H NMR (CDCl$_3$; ppm): 7.15 (m, 1H), 6.72 (m, 2H), 4.29 (m, 1H), 4.02 (d, 1H), 3.81 (s, 3H), 3.73 (s, 3H), 3.60–3.92 (m, 2H), 3.44 (m, 2H), 3.16 (dd, 1H), 2.50–3.10 (m, 4H), 2.33 (s, 3H), 1.97 (dd, 1H).

MS (SIMS; m/z): 372 (M+1)$^+$, 345, 340.

REFERENCE EXAMPLE 2

Synthesis of compound b

Compound a obtained in Reference Example 1 (500 mg) was dissolved in 10 ml of anhydrous methylene chloride, and a solution of 0.74 ml of titanium tetrachloride in 1 ml of methylene chloride was added dropwise under ice cooling. Ten minutes later, a solution of 0.25 ml of dichloromethyl methyl ether in 1 ml of methylene chloride was added dropwise under ice cooling, and the mixture was stirred under the same conditions for 130 minutes and then at room temperature for an additional 130 minutes. After ice water was added to the reaction mixture, stirring was continued for some time, and the aqueous layer was separated. 5N sodium hydroxide solution was added to adjust the pH to 7–7.5, followed by extraction with ethyl acetate. The extract was washed with saturated aqueous solution of sodium chloride and dried over anhydrous sodium sulfate. Evaporation of the solvent gave 530 mg of a crude product, which was purified by chromatography (Wako Gel C-200; hexane:ethyl acetate =2:1–1:1) to obtain 418 mg (77.7%) of compound b. At the same time, 98 mg (19%)

of the unreacted starting material (compound a) was recovered.

$^1$H NMR (CDCl$_3$; ppm): 10.02 (s, 1H), 7.70 (d, 1H, J=8.6Hz), 6.90 (d, 1H, J=8.6Hz), 4.31 (t, 1H, J=3.6Hz), 4.04 (d, 1H, J=2.9Hz), 3.91 (s, 3H), 3.76 (m, 1H), 3.76 (s, 3H), 3.69 (dd, 1H, J=16.6, 2.5Hz), 3.58 (dd, 1H, J=11.0, 4.4Hz), 3.54 (bs, 1H), 3.50 (m, 1H), 3.18 (dd, 1H, J=9.7, 5.6Hz), 2.99 (bd, 1H, J=11.7Hz), 2.69 (m, 1H), 2.65 (dd, 1H, J=16.5, 11.8Hz), 2.35 (s, 3H), 2.03 (dd, 1H, J=13.5, 9.7Hz).

$^{13}$C NMR (CDCl$^3$; ppm): 191.6, 175.7, 159.9, 139.3, 135.5, 126.6, 123.7, 117.6, 108.3, 70.1, 65.0, 64.5, 57.9, 57.4, 56.9, 55.8, 52.3, 42.8, 41.9, 29.1, 28.9.

IR (KBr; cm$^{-1}$) 3480, 1728, 1683, 1592, 1580, 1483, 1451, 1269.

MS (EI; m/z): 400 (M+1)$^+$, 369 (M+1-OMe).

REFERENCE EXAMPLE 3

Synthesis of compound c

Compound b obtained in Reference Example 2 (253 mg) was dissolved in 7 ml of methanol, and 88 mg of hydroxylamine hydrochloride was added. The mixture was stirred at room temperature for two hours and then concentrated. An NaHCO$_3$ solution was added to the concentrate, and the resulting mixture was extracted with ethyl acetate. The extract was washed with saturated aqueous solution of sodium chloride and dried over anhydrous sodium sulfate. Evaporation of the solvent gave 253 mg (96.4%) of compound c.

$^1$H NMR (CDCl$_3$; ppm): 8.31 (s, 1H), 7.51 (d, 1H), 6.76 (d, 1H), 4.30 (m, 1H), 4.03 (d, 1H), 3.82 (s, 3H), 3.75 (s, 3H), 3.10-3.80 (m, 3H), 3.49 (bs, 1H), 3.18 (dd, 1H), 2.47-3.13 (m, 4H), 2.34 (s, 3H), 2.00 (dd, 1H).

MS (EI; m/z): 415 (M+1)$^+$, 384 (M+1-OMe)$^+$.

REFERENCE EXAMPLE 4

Synthesis of compound d

Compound c obtained in Reference Example 3 (200 mg) was dissolved in 4 ml of acetic anhydride, and the solution was stirred at 130° C. for four hours. The reaction mixture was concentrated under reduced pressure, and the residue was dissolved in ethyl acetate. The resulting solution was washed with saturated NaHCO$_3$ solution and saturated aqueous solution of sodium chloride in that order, and dried over anhydrous sodium sulfate. Evaporation of the solvent gave 227 mg of a crude product, which was then purified by chromatography (Wako Gel C-200, 15 ml; hexane:ethyl acetate =2:1) to obtain 186 mg (88.0%) of compound d.

$^1$H NMR (CDCl$_3$; ppm): 7.57 (d, 1H), 6.82 (d, 1H), 4.30-4.50 (m, 2H), 3.85-4.07 (m, 2H), 3.89 (s, 3H), 3.78 (s, 3H), 3.47 (bs, 1H), 3.43 (m, 1H), 2.90-3.15 (m, 3H), 2.43-2.80 (m, 2H), 2.33 (s, 3H), 1.98 (s, 3H), 1.92 (m, 1H).

MS (EI; m/z): 438 M+, 407 (M-OMe)$^+$.

REFERENCE EXAMPLE 5

Synthesis of compound e

Compound obtained in Reference Example 2 (3.0 g) was dissolved in 50 ml of methanol. To the solution were added 1.28 ml of 30% hydrogen peroxide and 0.5 ml of concentrated sulfuric acid, and the mixture was stirred at room temperature for seven hours. After the reaction mixture was neutralized with saturated NaHCO$_3$ solution, methanol was distilled off, and the residue was extracted three times with ethyl acetate. The extract was washed with saturated aqueous solution of sodium chloride and dried over anhydrous sodium sulfate. Evaporation of the solvent gave 3.23 g of a crude product, which was then purified by chromatography (Wako Gel C-200, 600 ml; chloroform:ethanol=1:0-50:1) to obtain 2.40 g (82.5%) of compound e. At the same time, 329 mg (11%) of the unreacted starting material (compound b) was recovered.

$^1$H NMR (CDCl$_3$; ppm): 6.55 (s, 2H), 4.21 (m, 1H), 4.01 (d, 1H), 3.72 (s, 6H), 3.63-3.80 (m, 2H), 3.47 (m, 2H), 2.23-3.30 (m, 5H), 2.31 (s, 3H), 1.98 (dd, 1H).

MS (EI; m/z): 387 M+, 356 (M-OMe)$^+$.

REFERENCE EXAMPLE 6

Synthesis of compound f

DX-52-1 (15 g) was suspended in 150 ml of methylene chloride, and 150 ml of a methylene chloride solution of boron tribromide (50 g/200 ml) was added dropwise under cooling at −78° C. After stirring for 22 hours at temperatures from −78° C. to room temperature, the reaction mixture was again cooled to −78° C., and 100 ml of a methylene chloride solution of boron tribromide (25 g/200 ml) was added dropwise. The mixture was then stirred for 7 hours at temperatures from −78° C. to room temperature. Ice was added to the resulting mixture, and the pH of the aqueous layer was raised to 7.2 with an NaOH solution, followed by addition of 3.87 g of NaCN. The aqueous layer was separated, concentrated and subjected to chromatography [Diaion HP-20, 2l; water:methanol=1:0-9:1 (v/v)] to obtain 11.17 g of sodium salt of compound f. The product was dissolved in 80 ml of water, and hydrochloric acid was added to the solution to adjust the pH to 3.5. The precipitate formed was recovered by filtration and dried, whereby 10.4 g (76.6%) of compound f was obtained.

$^1$H NMR (D$_2$O, NaOD, PD=9.3; ppm): 7.13 (m, 1H), 6.75 (m, 2H), 4.24 (d, 1H, J=2.7Hz), 4.13 (m, 1H), 3.70 (m, 2H), 3.57 (m, 1H), 3.51 (bs, 1H), 3.10 (dd, 1H, J=10.0, 5.4Hz), 2.40-2.84 (m, 4H), 2.22 (s, 3H), 2.03 (dd, 1H, J=10.5, 13.2Hz).

$^{13}$C NMR (D$_2$O, NaOD, PD=9.3; ppm): 184.4, 154.6, 138.6, 128.9, 121.9, 120.1, 119.7, 114.8, 70.7, 65.0, 65.0, 58.6, 45.3, 41.9, 33.3 30.0.

MS (SIMS; m/z):
344 (M+1)$^+$.

REFERENCE EXAMPLE 7

Synthesis of compound g

Compound f obtained in Reference Example 6 (100 mg) was dissolved in 4 ml of acetic acid, and 39 μl of concentrated nitric acid was added, followed by stirring at room temperature for 150 minutes. Concentrated nitric acid (10 μl) was further added, and stirring was continued at room temperature for an additional 130 minutes. The reaction mixture was concentrated, and the concentrate was subjected to chromatography (Diaion HP-20, 10 ml; water:methanol=1:0-1:1) to obtain 40.3 mg (37.9%) of compound g.

$^1$H NMR (CD$_3$OD; ppm): 7.90 (d, 1H), 6.82 (d, 1H), 4.34 (m, 2H), 3.40-3.96 (m, 5H), 2.52-3.24 (m, 4H), 2.34 (s, 3H), 2.14 (m, 1H).

IR (KBr; cm-1): 3400, 1588, 1520, 1340, 1303.

MS (SIMS: m/z): 389 (M+1)$^+$.

REFERENCE EXAMPLE 8

Synthesis of compound h

Compound g obtained in Reference Example 7 (200 mg) was dissolved in 3 ml of methanol. An ethereal solution of diazomethane was slowly added to the solution until evolution of nitrogen gas ceased, and the resulting mixture was stirred at room temperature for one hour. After complete consumption of compound g was confirmed by TLC, the reaction mixture was concentrated, and the concentrate was subjected to chromatography (Wako Gel C-200, 35 ml: chloroform:methanol=1:0–100:1) to obtain 162 mg (75.5%) of compound h.

$^1$H NMR (CDCl$_3$; ppm): 7.98 (d, 1H), 6.82 (d, 1H), 4.30 (m, 1H), 4.03 (d, 1H), 3.92 (s, 3H), 3.79 (s, 3H), 3.40–3.87 (m, 3H), 3.50 (bs, 1H), 2.50–3.30 (m, 5H), 2.33 (s, 3H), 2.00 (dd, 1H).

$^{13}$C NMR (CDCl$_3$; ppm): 175.6, 159.4, 142.3, 133.5, 125.9, 124.5, 117.5, 108.3, 70.0, 65.0, 64.6, 58.0, 57.5, 56.8, 56.2, 52.4, 42.8, 41.9, 30.4, 29.1.

IR (KBr; cm$^{-1}$): 3400, 1726, 1603, 1584, 1514, 1472, 1443, 1346, 1297, 1275.

MS (EI; m/z): 416 M$^+$, 385 (M-OMe)$^+$.

REFERENCE EXAMPLE 9

Synthesis of compound j

Compound h obtained in Reference Example 8 (257 mg) was dissolved in 5 ml of methanol. To the solution were added 1.5 ml of 1N hydrochloric acid and 80 mg of 5% Pd-C, and the mixture was stirred at room temperature for 4.5 hours under a hydrogen gas stream. The catalyst was filtered off, and the filtrate was concentrated to obtain 247 mg of a crude hydrochloride of compound i. Acetic anhydride (4 ml) was added to this hydrochloride, and the mixture was stirred at room temperature for 15 hours. The reaction mixture was then concentrated and an NaHCO$_3$ solution was added to the concentrate, followed by extraction with ethyl acetate. The extract was washed with saturated aqueous solution of sodium chloride and dried over anhydrous sodium sulfate. Evaporation of the solvent gave 212 mg of a crude product, which was then subjected to chromatography (Wako Gel C-200, 30 ml; hexane:ethyl acetate =1:2–0:1) to obtain 75 mg (25.8%) of compound j.

$^1$H NMR (CDCl$_3$; ppm): 7.18 (d, 1H), 6.70 (d, 1H), 4.25–4.47 (m, 2H), 3.90–4.07 (m, 2H), 3.81 (s, 3H), 3.73 (s, 3H), 3.45 (m, 2H), 2.83–3.17 (m, 2H), 2.40–2.80 (m, 3H), 2.31 (s, 3H), 2.15 (s, 3H), 2.01 (s, 3H), 1.99 (m, 1H).

IR (KBr; cm$^{-1}$): 1736, 1731, 1664, 1602, 1486, 1266, 1231.

MS (EI; m/z): 471 (M+1)$^+$, 440 (M+1-OMe)$^+$.

REFERENCE EXAMPLE 10

Injection

Compound 2 (0.1 g) and glucose (50 g) were dissolved in distilled water to make 1 liter of solution. The solution was filtered through a membrane filter with pore size of 0.22 μ (Millipore Inc., FGLD14200) under a nitrogen gas pressure of 0.5 kg/cm$^2$. The filtrate was poured in 20 ml-white ampules (10 ml in each), and each ample was sealed in a conventional manner to prepare injections.

We claim:

1. Derivatives of DC-52 represented by the formula:

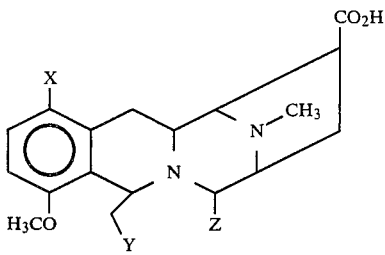

wherein X is chlorine, bromine, iodine, hydroxyl, formyl, hydroxyiminomethyl, cyano, nitro, amino or lower alkanoylamino; and Y is hydroxyl and Z is cyano, and pharmacologically acceptable salts thereof.

* * * * *

UNITED STATES PATENT AND TRADEMARK OFFICE
CERTIFICATE OF CORRECTION

PATENT NO. : 4,879,386

DATED : November 7, 1989

INVENTOR(S) : HIROMITSU SAITO ET AL.

It is certified that error appears in the above-identified patent and that said Letters Patent is hereby corrected as shown below:

ON THE TITLE PAGE,
AT [57] ABSTRACT

"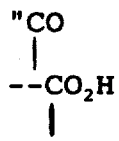  (I)" should read  (I)--.

COLUMN 1

Line 2, "ANTI-TUMOR DC-52 COMPOUNDSc1" should read --ANTI-TUMOR DC-52 COMPOUNDS--.

Line 21, " 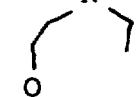 " should read -- 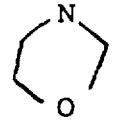 --.

Line 53, "CO  (I)" should read (I)--.
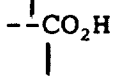

COLUMN 7

Line 63, " 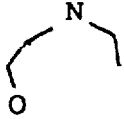 " should read -- 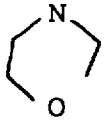 --.

COLUMN 9

Line 43, "Five day mice" should read --Five ddy mice--.

UNITED STATES PATENT AND TRADEMARK OFFICE
CERTIFICATE OF CORRECTION

PATENT NO. : 4,879,386

DATED : November 7, 1989

INVENTOR(S) : HIROMITSU SAITO ET AL.

It is certified that error appears in the above-identified patent and that said Letters Patent is hereby corrected as shown below:

COLUMN 10

Line 63, "<Sodium" should read --Sodium--.

COLUMN 11

Line 9, "2.07 (dd, 1H." should read --2.07 (dd, 1H).--.

COLUMN 12

Line 33, "(CD30D: ppm):" should read --($CD_3OD$: ppm): --.

COLUMN 13

Line 22, "water:menthanol=0-3:2)" should read
        --water:menthanol=1:0-3:2)--.
    Line 24, "(D20; ppm):" should read --($D_2O$; ppm):--.

COLUMN 14

Line 31, "sodium 1H NMR (D20; ppm):" should read
        --sodium salt.
           $^1H$ NMR ($D_2O$; ppm):--.

COLUMN 15

Line 14, "($D^2O$; ppm):" should read --($D_2O$; ppm):--.

COLUMN 16

Line 29, "in of" should read --in 15 mℓ of--.
    Line 33, "for hours." should read --for 15 hours.--.

UNITED STATES PATENT AND TRADEMARK OFFICE
CERTIFICATE OF CORRECTION

PATENT NO. : 4,879,386

DATED : November 7, 1989

INVENTOR(S) : HIROMITSU SAITO ET AL.

It is certified that error appears in the above-identified patent and that said Letters Patent is hereby corrected as shown below:

COLUMN 17

Line 60, "Compound" should read --Compound b--.

Signed and Sealed this

Seventeenth Day of March, 1992

Attest:

HARRY F. MANBECK, JR.

*Attesting Officer*  *Commissioner of Patents and Trademarks*